United States Patent
Hannah

(10) Patent No.: US 6,767,731 B2
(45) Date of Patent: Jul. 27, 2004

(54) ELECTRON INDUCED FLUORESCENT METHOD FOR NUCLEIC ACID SEQUENCING

(75) Inventor: Eric C. Hannah, Pebble Beach, CA (US)

(73) Assignee: Intel Corporation, Santa Clara, CA (US)

( * ) Notice: Subject to any disclaimer, the term of this patent is extended or adjusted under 35 U.S.C. 154(b) by 190 days.

(21) Appl. No.: 09/940,228

(22) Filed: Aug. 27, 2001

(65) Prior Publication Data

US 2003/0039978 A1 Feb. 27, 2003

(51) Int. Cl.[7] .............................................. C12M 1/34
(52) U.S. Cl. .............................. 435/287.2; 435/288.5; 435/288.6; 435/288.7; 204/403.13; 204/603
(58) Field of Search ........................... 422/82.05, 82.08; 435/287.2, 288.5, 288.6, 288.7; 204/403.13, 603; 313/306, 309

(56) References Cited

U.S. PATENT DOCUMENTS

| | | | |
|---|---|---|---|
| 5,079,169 A | 1/1992 | Chu et al. | |
| 5,202,231 A | 4/1993 | Drmanac et al. | |
| 5,332,666 A | 7/1994 | Prober et al. | |
| 5,436,130 A | 7/1995 | Mathies et al. | |
| 5,776,674 A | 7/1998 | Ulmer | |
| 5,821,060 A | 10/1998 | Arlinghaus et al. | |
| 5,846,727 A | 12/1998 | Soper et al. | |
| 5,972,619 A | 10/1999 | Drmanac et al. | |
| 6,018,041 A | 1/2000 | Drmanac et al. | |
| 6,025,136 A | 2/2000 | Drmanac | |
| 6,045,996 A | 4/2000 | Cronin et al. | |
| 6,063,573 A | 5/2000 | Kayyem | |
| 6,083,695 A | 7/2000 | Hardin et al. | |
| 6,136,543 A | 10/2000 | Anazawa et al. | |
| 6,188,167 B1 | 2/2001 | Endo et al. | |
| 6,225,068 B1 | 5/2001 | Wolfrum | |
| 6,232,062 B1 | 5/2001 | Kayyem et al. | |
| 6,238,871 B1 | 5/2001 | Köster | |
| 6,447,724 B1 * | 9/2002 | Jensen et al. .............. 422/68.1 |

FOREIGN PATENT DOCUMENTS

| | | |
|---|---|---|
| WO | WO 99/57321 | 11/1999 |
| WO | WO 00/36152 | 6/2000 |
| WO | WO 01/18246 | 3/2001 |
| WO | WO 01/34302 | 5/2001 |

OTHER PUBLICATIONS

Burns, Mark A. et al., "Microfabricated structures for integrated DNA analysis", Proc. Natl. Acad. Sci., 93:5556–5561, May 1996.

(List continued on next page.)

Primary Examiner—David A. Redding
(74) Attorney, Agent, or Firm—Blakely, Sokoloff, Taylor & Zafman LLP

(57) ABSTRACT

An apparatus, compositions and related methods for sequencing a target nucleic acid are described. In certain embodiments, the apparatus is a microfluidic apparatus comprising an input chamber, microchannel, output chamber and a detection unit that is operatively connected to the microchannel. In preferred embodiments, the methods include hybridizing a target nucleic acid to one or more probe libraries, moving the hybridized target nucleic acid past the detector, and detecting bound probes. Probe libraries may comprise oligonucleotides or oligonucleotide analogs, preferably with each probe uniquely labeled. A linear order of labeled probes hybridized to the target nucleic acid can be detected and the target nucleic acid sequence deduced. In preferred embodiments, probe labels are detected by analysis of electron-induced fluorescence of probes labeled with conductive polymers.

13 Claims, 4 Drawing Sheets

OTHER PUBLICATIONS

Knight, James B. et al., "Hydrodynamic Focusing on a Silicon Chip: Mixing Nanoliters in Microseconds", *Physical Review Letters*, 80(17):3863–3866, Apr. 1998.

Machara, Nicholas P. et al., "Efficient detection of single molecules eluting off an optically trapped microsphere", *Bioimaging*, 6:33–42, 1998.

Chou, Hou–Pu et al., "A Microfabricated device for sizing and sorting DNA molecules", *Proc. Natl. Acad. Sci.*, 96:11–13, 1999.

Chen, Liaohai et al., "Highly sensitive biological and chemical sensors based on reversible fluorescence quenching in a conjugated polymer", *PNAS*, 96(22):12287–12292, Oct. 1999.

Meller, Amit et al., "Rapid nanopore discrimination between single polynucleotide molecules", *PNAS*, 97(3):1079–1084, Feb. 2000.

Rusu, Cristina et al., "Fabrication of micromachined pipettes in a flow channel for single molecule handling of DNA", *Proceedings MEMS*, Japan, 2000.

Schafer, Burk et al., "Single molecule DNA restriction analysis in the light microscope", *Single Molecules*, 1:33–40, 2000.

Chen, Liaohai et al., "Tuning the properties of conjugated polyelectrolytes through surfactant complexation", *Journal American Chemical Society*, Apr. 2000.

Baumann, Christoph G. et al., "Stretching of single collapsed DNA molecules", *Biophysical Journal*, 78:1965–1978, Apr. 2000.

Hegner, Martin, "DNA handles for single molecule experiments", *Single Molecules*, 1(2):139–144, 2000.

Huser, Thomas et al., "Single chain spectroscopy of conformational dependence of conjugated polymer photophysics", *PNAS*, 97(21)11187–11191, Oct. 2000.

Tretiak, S. et al., "CEO/semiempirical calculations of UV–visible spectra in conjugated molecules", *Chemical Physics Letters*, 331:561–568, Dec. 2000.

* cited by examiner

ELECTRON INDUCED FLUORESCENT METHOD FOR NUCLEIC ACID SEQUENCING

BACKGROUND OF THE INVENTION

1. Field of the Invention

The present invention relates to the fields of molecular biology and nucleic acid analysis. In particular, the invention relates to methods, composition and apparatus for electron-induced fluorescent DNA sequencing.

2. Background

With the advent of the human genome project, a need developed for improved methods of sequencing nucleic acids such as DNA and RNA. Genetic information is stored in the form of very long molecules of deoxyribonucleic acid (DNA), organized into chromosomes. The twenty-three pairs of chromosomes in the human genome contain approximately three billion bases of DNA sequence. This DNA sequence information determines multiple characteristics of each individual, such as height, eye color and ethnicity. Many common diseases, such as cancer, cystic fibrosis, sickle cell anemia and muscular dystrophy are based at least in part on variations in DNA sequence.

Determination of the entire sequence of the human genome has provided a foundation for identifying the genetic basis of such diseases. However, a great deal of work remains to be done to identify the genetic variations associated with each disease. This requires DNA sequencing of portions of chromosomes in individuals or families exhibiting each such disease, in order to identify specific changes in DNA sequence that promote the disease. Ribonucleic acid (RNA), an intermediary molecule required for processing of genetic information, can also be sequenced to identify the genetic basis of various diseases.

Existing methods for nucleic acid sequencing, based on detection of fluorescently labeled nucleic acids that have been separated by size, are limited by the length of the nucleic acid that can be sequenced. Typically, only 500 to 1,000 bases of nucleic acid sequence can be determined at one time. This is much shorter than the length of the functional unit of DNA, referred to as a gene, which can be tens or even hundreds of thousands of bases in length. Determination of a complete gene sequence requires that many copies of the gene be produced, cut into overlapping fragments and sequenced, after which the overlapping DNA sequences can be assembled into the complete gene. This process is laborious, expensive, inefficient and time-consuming.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Definitions

As used herein, "a" or "an" may mean one or more than one of an item.

As used herein, the term "about" when applied to a number means within plus or minus three percent of that number. For example, "about 100" means any integer between 97 and 103.

"Nucleic acid" encompasses DNA, RNA, single-stranded, double-stranded or triple stranded and any chemical modifications thereof, although single-stranded nucleic acids are preferred. Virtually any modification of the nucleic acid is contemplated by this invention.

Within the practice of the present invention, a "nucleic acid" may be of almost any length, from 10, 20, 50, 100, 200, 300, 500, 750, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 2,000,000, 5,000,000 or even more bases in length, up to a full-length chromosomal DNA molecule.

The apparatus, compositions and methods described herein can be used to sequence large complex genomes. Advantageously, intensive manual procedures involving size fractionation of nucleic acid fragments on polyacrylamide gels are avoided. The apparatus, compositions and methods can provide high speed, small quantity, long read length nucleic acid sequencing. Information about a biological agent or a patient may be obtained in a timely and cost effective manner. The information obtained from the nucleic acid sequence may be used to determine and initiate effective countermeasures, such as vaccine administration, antiviral administration, patient monitoring, or treatment.

In certain embodiments a small quantity of a target nucleic acid to be sequenced may be hybridized with a probe library or a plurality of probe libraries. Probe libraries can be a group of oligonucleotides or oligonucleotide analogs. In preferred embodiments, each probe in a library is uniquely and detectably labeled. By identifying the probes hybridized to a target nucleic acid, the linear order of probes can be analyzed and a nucleic acid sequence determined for the target. In certain embodiments, analysis of a target nucleic acid molecule(s) hybridized to a series of probes can entail monitoring the target nucleic acid using a detection unit operatively connected to a microfluidic apparatus. In particular embodiments one or more microfluidic chambers, channels, capillaries, pores, valves or combinations thereof may be used to process, move, and/or position a target nucleic acid for analysis. A microfluidic device may be designed to position a nucleic acid molecule(s) in an extended conformation for analysis. In certain embodiments, the target nucleic acid may be manipulated so that only a single target nucleic acid molecule moves along a microchannel at a time.

Figure 1:
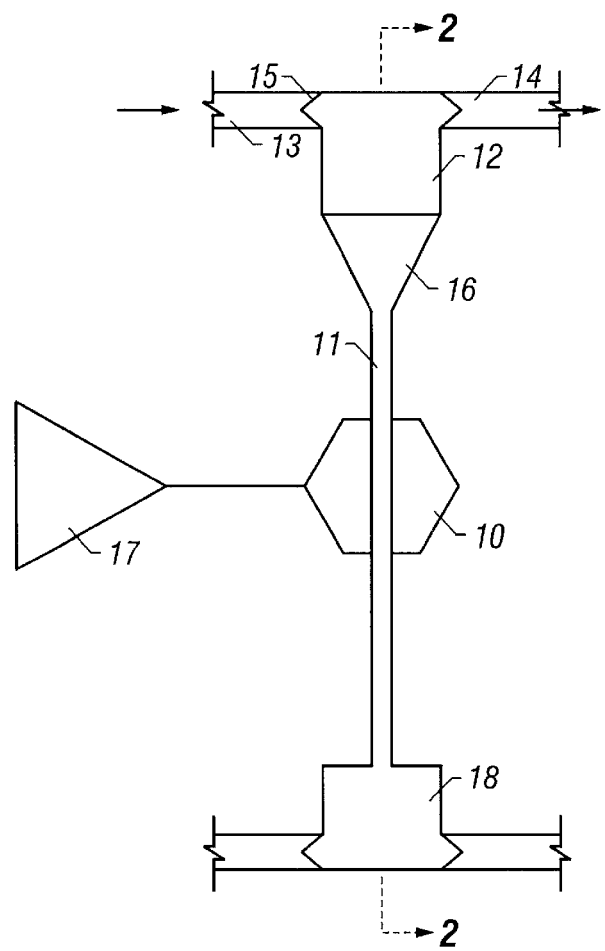
FIG. 1 illustrates an embodiment of a microfluidic device.

FIG. 1 illustrates an exemplary embodiment of an apparatus that may be used in the practice of certain methods of the invention. A detection unit 1 may be positioned to monitor target nucleic acid molecules flowing through a channel 2. The apparatus will typically include an input or reaction chamber 3 where one or more target nucleic acids may be hybridized to a probe library. An input chamber 3 may have an inlet port 4 and an outlet port 5 to provide for the flow of reagents. Flow in and out of input chamber 3 can be controlled by microvalves 6 and the like operatively connected to the inlet port 4 and outlet port 5.

A focusing region 7 may be used to hydrodynamically focus fluids containing hybridized target nucleic acid(s). Hydrodynamic focusing may separate one or more target nucleic acid molecules as fluid flows from an input chamber 3 to a channel 2. As a target molecule moves through a focusing region 7 it is extended to an approximate linear conformation.

A channel 2 may be positioned to flow fluid or solutions by a detection unit 1. A detection unit 1 will typically detect the spectral signature of each labeled probe, preferably in sequential order. A detection unit 1 may be operatively connected to a data processing system 8 for storage and analysis of detected spectra.

The channel 2 will have a lumen or groove that is in fluid communication with a fluid focusing region and an output chamber 9. An output chamber 9 may be used for collecting or sorting fluids flowing out of channel 2. An output chamber 9 may also be operatively connected to means for producing a motive force for fluid flow. Means for producing a motive force include but are not limited to thermal, electroosmotic, pressure, and/or vacuum gradients.

Figure 2:
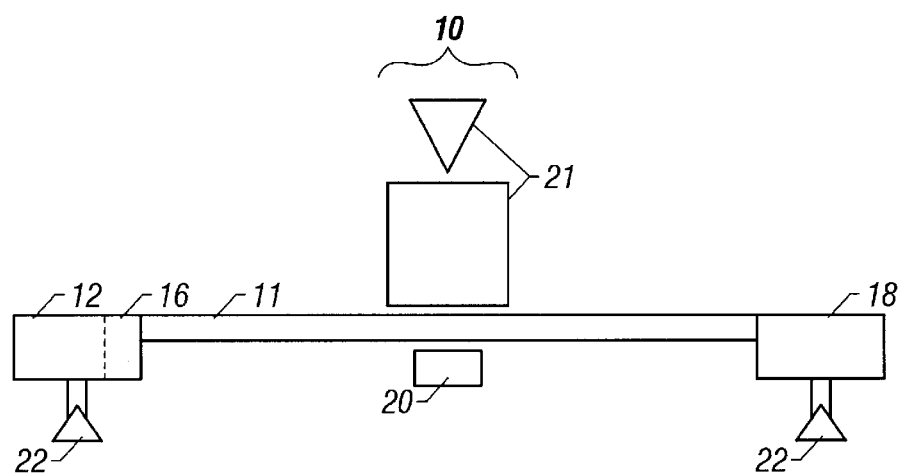
FIG. 2 illustrates a cross-sectional view along the line 2—2 in FIG. 1.

FIG. 2 illustrates a cross-sectional view of the apparatus of FIG. 1 along the line 2—2. The illustration in FIG. 2 shows an input chamber 3 in fluid communication with a channel 2. The channel 2 is in fluid communication with an output chamber 9. The channel 2 may be positioned adjacent to a detector 20 which is part of the detection unit 1. Included in the detection unit 1 can be an excitation source 21, preferably a micro electron beam column. In certain embodiments the detector may be operatively connected to a data processing system. Also illustrated in the cross-sectional view are fluid control means 22. The fluid control means 22 may be sources of pressure, vacuum, heat, cooling, electric potential or other gradients to control the flow of fluids within the apparatus. The excitation source 21 may be positioned to provide excitation energy to labeled probes as they flow in the channel 2. Energy from the excitation source 21 may be absorbed by a labeled probe molecule and portions of that energy may be emitted from the label as a detectable signal, preferably a label specific spectral signal.

Figure 3:
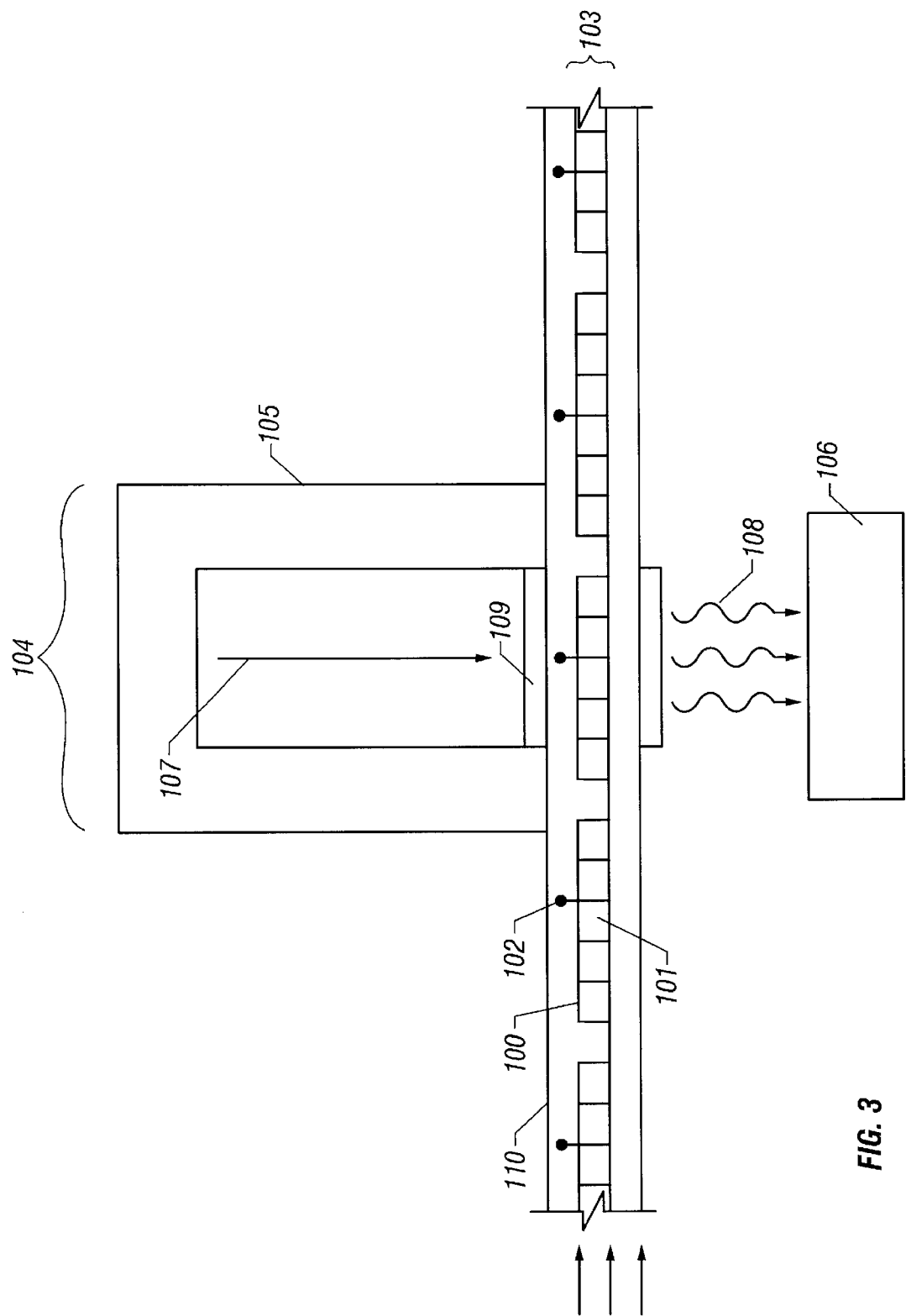
FIG. 3 illustrates an embodiment of a detection unit.

FIG. 3 illustrates an expanded view of a signal-monitoring portion of an exemplary apparatus. In one embodiment, one or more probes 30 are associated with the target nucleic acid molecule(s) 31 in a sequence specific manner, preferably by Watson-Crick base pairing, forming a double-stranded hybridized nucleic acid 33. In certain embodiments one or more labels 32 uniquely identify each probe 30. A probe may be detected as it moves past detection unit 34. In preferred embodiments, individual probes 30 are detected in sequential order as they move past detection unit 34 in a linear sequence, corresponding to the linear sequence of the target nucleic acid 31.

Detection unit 34 is generally comprised of an excitation source 35 and a detector 36. In one embodiment the excitation source 35 comprises a micro electron beam device or a micro e-beam 37. The micro e-beam 37 may be focused to pass through a window 39 in the channel 40 and within an appropriate distance of a probe 30 in order to excite the probe 30 and transfer energy to a label 32 attached to the probe 30 by coulombic induction. An excited label 32 subsequently emits a signal 38 that is monitored by a detector 36. Preferably the signal 38 is an emission spectrum unique to the particular label 32. In certain embodiments, the time of each probe 30 passing a detector 36 is determined and recorded. Thus, if a hybridized nucleic acid 33 is passing a detector 36 at a constant speed (nucleotide per time unit), gaps in a probe hybridization pattern can be detected. Such gaps may occur where hybridization between the target nucleic acid 31 and the library of probes 30 is incomplete. Hybridization gaps can be addressed by using multiple hybridizations with multiple pools of probes 30 or by analyzing a plurality of target nucleic acid molecules 33 that have been hybridized to one or more probe libraries.

Figure 4:
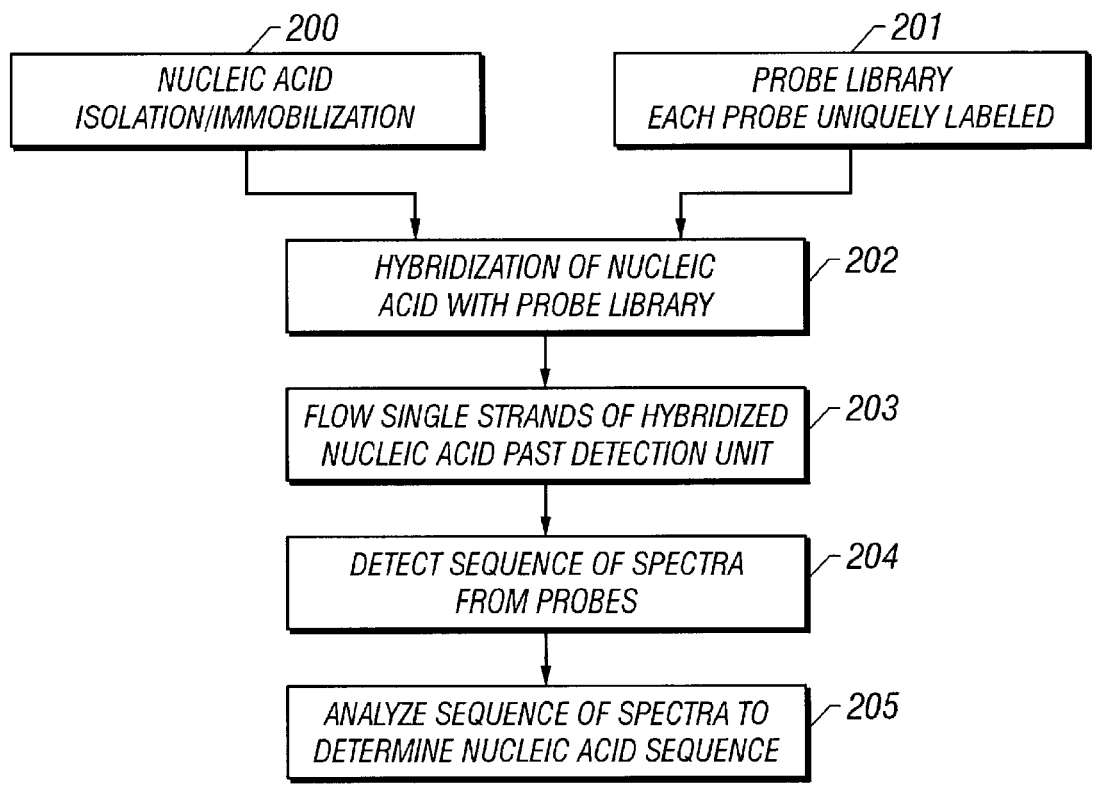
FIG. 4 is a flow chart illustrating an embodied method.

FIG. 4 is a flow chart representing an exemplary method. Block 200 represents the isolation or immobilization of a target nucleic acid that is a candidate for sequencing. Block 201 represents the synthesis of a probe library, including the attachment of a unique label to each probe of the library. Block 202 represents the mixing and hybridization of a target nucleic acid solution and a probe library, preferably within an input chamber of a microfluidic device. Block 203 represents the moving of a hybridized nucleic acid in a channel past a detection unit. Block 204 represents the detection of signals produced by labels attached to probes that are hybridized to a target nucleic acid. An excitation source, preferably an electron beam, is used to excite a label resulting in the emission of a signal as the label returns to its ground state. The analysis of the signals detected is represented in block 205. The signals that are detected by a detector can be analyzed by a data processing system. Analysis typically entails the compilation of data sets, the determination of temporal occurrence of each spectrum, and an assignment of probe sequence to each spectrum resulting in a linear nucleic acid sequence.

In certain embodiments one or more hybridized target nucleic acid molecules can be analyzed sequentially, concurrently or in parallel. In one embodiment hybridized target nucleic acids may be passed by the detection unit sequentially, that is, one nucleic acid at a time. In another embodiment a plurality of nucleic acids may be passed by a detection unit concurrently, that is, more than one at a time. In still other embodiments hybridized target nucleic acid may be analyzed sequentially or concurrently in parallel processing using an array of microfluidic devices fabricated on a single surface. The data obtained can be converted into a nucleic acid sequence by statistical analysis and processing of the signals detected by a data processing system.

Following detection and analysis by the described methods, one may compare the nucleic acid sequence determined for a given sample or patient with a statistically significant reference group of organisms or normal patients and patients exhibiting a disease. In this way, it is possible to correlate characteristics of the nucleic acids with various organisms or clinical states. The skilled artisan will understand that random sequencing of the total genomic DNA of a sample or individual is not a particularly efficient way in which to identify or detect DNA markers for a disease state or physiological condition. Typically, mapping or linkage studies are performed, in some cases in a family of related individuals exhibiting a high occurrence of a disease state or condition, in order to identify a portion of a chromosome associated with the state or condition. That portion of chromosomal DNA may be targeted for analysis by the sequencing methods of the present invention, preferably by isolating the nucleic acid segment of interest prior to sequencing.

Target Nucleic Acids

Nucleic acid molecules to be sequenced (target nucleic acids) may be prepared by any standard technique. In one embodiment, the nucleic acids may be naturally occurring DNA or RNA molecules. Virtually any naturally occurring nucleic acid may be prepared and sequenced by the methods of the present invention including, without limit, chromosomal, mitochondrial or chloroplast DNA or messenger, heterogeneous nuclear, ribosomal or transfer RNA.

Methods for preparing and isolating various forms of cellular nucleic acids are known. In general cells, tissues or other source material containing nucleic acids to be sequenced must first be homogenized, for example by freezing in liquid nitrogen followed by grinding in a morter and pestle. Certain tissues may be mechanically homogenized using a Waring blender, Virtis homogenizer, Dounce homogenizer or other homogenizer. Crude homogenates may be extracted with detergents, such as sodium dodecyl sulphate (SDS), Triton X-100, CHAPS, octylglucoside or other detergents known in the art. Alternatively or in addition, extraction may use chaotrophic agents such as guanidinium isothiocyanate, or organic solvents such as phenol. In some embodiments, protease treatment, for example with proteinase K, may be used to degrade cell proteins. Particulate contaminants may be removed by centrifugation. Dialysis against aqueous buffer of low ionic strength may be of use to remove salts or other soluble contaminants. Nucleic acids may be precipitated by addition of ethanol at −20° C., or by addition of sodium acetate (pH 6.5) to a final concentration of 0.3 M and 0.8 volumes of 2-propanol. Precipitated nucleic acids may be collected by centrifugation or, for chromosomal DNA, by spooling the precipitated DNA with a glass pipet.

The procedures listed above are exemplary only and that many variations may be used within the scope of the present invention, depending on the particular type of target nucleic acid. For example, mitochondrial DNA is often prepared by cesium chloride density gradient centrifugation, using step gradients, while mRNA is often prepared using preparative columns from commercial sources, such as Promega (Madison, Wis.) or Clontech (Palo Alto, Calif.).

Depending on the type of nucleic acid to be prepared various nuclease inhibitors may be required. For example, RNase contamination in bulk solutions may be eliminated by treatment with diethyl pyrocarbonate (DEPC), while commercially available nuclease inhibitors may be obtained from standard sources such as Promega (Madison, Wis.) or BRL (Gaithersburg, Md.). Purified nucleic acid may be dissolved in aqueous buffer, such as TE (Tris-EDTA) and stored at −20° C. or in liquid nitrogen prior to use.

In cases where single stranded DNA (ssDNA) is to be sequenced, an ssDNA may be prepared from double stranded DNA (dsDNA) by standard methods. Most simply, dsDNA may be heated above its annealing temperature, at which point it spontaneously disaggregates into ssDNA. Representative conditions might involve heating at 92 to 95° C. for 5 min or longer.

Although the discussion above concerns preparation of naturally occurring nucleic acids virtually any type of nucleic acid that is able to hybridize with a probe library of the invention could potentially be sequenced by the methods of the present invention. For example, nucleic acids prepared by various standard amplification techniques, such as polymerase chain reaction (PCR™) amplification, could be sequenced within the scope of the present invention.

Target nucleic acid templates may be isolated from a wide variety of organisms including, but not limited to, viruses, bacteria, eukaryotes, mammals, and humans. In certain embodiments target nucleic acid(s) that are isolated and amplified via cloning into plasmids, M13, lambda phage, P1 artificial chromosomes (PACs), bacterial artificial chromosomes (BACs), yeast artificial chromosomes (YACs) and other cloning vectors may be sequenced using the methods of the invention. Also contemplated for use are amplified nucleic acids or amplified portions of nucleic acids. In specific embodiments a cloning vector can be linearized, immobilized, denatured and hybridized with a set(s) of probe libraries.

Nucleic Acid Amplification

Nucleic acids that may be used as templates for amplification are typically isolated from cells contained in biological samples according to standard methodologies. The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

A number of template dependent processes are available to amplify target nucleic acid sequences present in a given sample. One of the best-known amplification methods is the polymerase chain reaction (PCR). Another method for nucleic acid amplification is the ligase chain reaction ("LCR"). In yet another method of nucleic acid amplification Qbeta Replicase may also be used. Strand Displacement Amplification (SDA) is another method of carrying out isothermal amplification of nucleic acids that involves multiple rounds of strand displacement and synthesis, i.e., nick translation. Other nucleic acid amplification procedures include transcription-based amplification systems (TAS), including nucleic acid sequence based amplification (NASBA) and 3SR.

Probe Libraries

The term "probe" denotes a defined nucleic acid segment such as DNA or RNA, or any analog thereof, such as peptide nucleic acid (PNA), which can be used to identify a specific complementary nucleic acid sequence in a target nucleic acid.

In certain embodiments one or more probe libraries may be prepared for hybridization to one or more target nucleic acid molecules. For example, a set of relatively short probes containing all 4096 or about 2000 non-complementary 6-mers, or all 16,384 or about 8,000 non-complementary 7-mers may be used. A set or plurality of subsets of 8-mers and longer probes may be used that include 65,536 or about 32,000 non-complementary 8-mers. If non-complementary subsets of probes are to be used a plurality of hybridizations and sequence analyses may be carried out and the results of the analyses merged into a single data set by computational methods. For example, if a library comprising only non-complementary 6-mers were used for hybridization and sequence analysis, a second hybridization and analysis using the same target nucleic acid molecule hybridized to those probe sequences excluded from the first library would be performed.

In certain preferred embodiments, the probe library contains all possible nucleic acid sequences for a given probe length (e.g., a six-mer library would consist of 4096 probes). In such cases, certain probes will form hybrids with complementary probe sequences. Such probe—probe hybrids, as well as unhybridized probes, may be excluded from the channel leading to the detection unit.

Methods for the selection and generation of complete sets or specific subsets of probes of all possible sequences for a given probe length are known. In general, for a probe of length "n", a complete set of all possible probe sequences can be represented as $4^n$ probes. As the probe length increases so does the number of distinct label moieties needed to uniquely label each probe. Limiting the number of label molecules required would involve the use of the shortest possible probe length consistent with the requirements for stable probe hybridization to the target molecule. In various embodiments, probes of 2, 3, 4, 5, 6, 7, 8, 9, 10, 11, 12, 13, 14, 15 or more nucleotides in length may be used within the scope of the present invention. The length of a probe(s) will vary with hybridization, wash conditions and composition of probe library or libraries used. Generally, probes may range from about 2 to about 20 monomers in length, with from about 4 to about 15 being preferred and from about 6 to about 10 being more preferred.

In certain embodiments, it may be useful to use probes comprising a random nucleic acid sequence in the middle of the probe and a constant nucleic acid sequences at one or both ends, a random portion and constant portion, respectively. This may be of use, for example, where the number of distinct label moieties available is lower than the number of possible probe sequences required for a probe length that is optimal for hybridization. For example, a subset of 12-mer probes could consist of a complete set of random 8-mer sequences attached to constant 2-mers at each end. Alternatively, a subset of 10-mer probes could consist of a complete set of random 8-mers attached to constant 1-mers at each end, or constant 2-mers at one end. These probe libraries can be subdivided according to their constant portions and hybridized separately to a target nucleic acid followed by analysis using the combined data of each different probe library to determine the nucleic acid sequence. The skilled artisan will realize that the number of sublibraries required will be a function of the number of constant bases that are attached to the random sequences. For example, with one constant base attached to the random sequences a total of four sublibraries might be hybridized to the target. For two constant bases attached to the random sequences, a total of sixteen sublibraries might be hybridized to the target, one for each possible contant region.

An alternative embodiment may use multiple hybridizations and analyses with a single probe library containing a specific constant portion attached to random probe sequences. For any given site on a target nucleic acid, it is possible that multiple probes of different, but overlapping sequence could bind to that site in a slightly offset manner. Thus, using multiple hybridizations and analyses with a single library, a complete sequence of the target nucleic acid could be obtained by compiling the overlapping, offset probe sequences. Although this approach is somewhat similar to the "shotgun" methods used with standard sequencing, it avoids having to generate and clone multiple restricted fragments for sequencing, since only a single target nucleic acid sequence is required. Random nucleic acid sequences of a probe may include, but are not limited to 2, 3, 4, 5, 6, 7, 8, 9, 10, 11, 12 or more bases.

Each probe may have at least one covalently attached label or tag. In certain embodiments the probes may have a plurality of attached labels or tags, the combination of which is unique to a particular probe. Combinations of labels can be used to expand the number of unique labels available for specifically identifying a probe in a library. In other embodiments the probes may each have a single unique label attached. Probes with a single label as well as probes with a plurality of labels are contemplated. The only requirement is that the signal detected from each probe must be capable of uniquely identifying the sequence of that probe.

1. Oligonucleotide Libraries

In certain embodiments of the invention the probe library is an oligonucleotide probe library. Oligonucleotide probes may be prepared by standard synthetic methods. Alternatively, probes can be purchased from a variety of vendors or synthesized on instrumentation such as the Applied Biosystems 381A DNA synthesizer (Foster City, Calif.) or similar instruments. In certain embodiments, probes may be labeled with fluorescent dyes or other types of labels. In preferred embodiments conductive polymers may be used to label oligonucleotide probes. In embodiments where probes are chemically synthesized, the label moiety may be covalently attached to one or more of the nucleotide precursors used for synthesis. Alternatively, the label may be attached after the probe has been synthesized.

In various embodiments, the sequence of the probe may be known before the label is attached, or the probe sequence attached to a given label may be identified after attachment. For example, a nucleic acid chip containing sequences complementary to all possible probe sequences may be designed, each sequence assigned to a given location on the chip. After hybridization to a library of labeled probes, the emission spectrum of the label at each position on the chip may be identified.

2. Peptide Nucleic Acids (PNAs)

In alternative embodiments peptide nucleic acids (PNAs) may be used as probes. PNAs are a polyamide type of DNA analog with monomeric units for adenine, guanine, thymine, and cytosine. PNAs are available commercially from companies such as Perceptive Biosystems. The backbone is made from repeating N-(2-aminoethyl)-glycine units linked by peptide bonds. The different bases (purines and pyrimidines) are linked to the backbone by methylene carbonyl linkages. Unlike DNA or other DNA analogs, PNAs do not contain any pentose sugar moieties or phosphate groups.

PNA synthesis may be performed with 9-fluoroenylmethoxycarbonyl (Fmoc) monomer activation and coupling using O-(7-azabenzotriazol-1-yl)-1,1,3,3-tetramethyluronium hexafluorophosphate (HATU) in the presence of a tertiary amine, N,N-diisopropylethylamine (DIEA). PNAs can be purified by reverse phase high performance liquid chromatography (RP-HPLC) and systematically verified by matrix assisted laser desorption ionization—time of flight (MALDI-TOF) mass spectrometry analysis.

Labeling of Probes

In certain embodiments one or more labels may be attached to each probe. The label will typically produce a detectable signal. Non-limiting examples of labels that could be used include fluorescent, luminescent, radioactive, phosphorescent, chemiluminescent, enzymatic, spin, electron dense, or mass spectroscopic labels. A label may be detected by using a variety of means, such as a spectrophotometer, luminometer, NMR (nuclear magnetic resonance), mass-spectroscopy, imaging systems, photomultiplier tube and/or other appropriate standard detection means. In certain embodiments conductive polymers may be used as a label. Conductive polymers are tunable to unique spectroscopic profiles based on the polymer composition, length, side chain groups and/or dopants.

Labels may be coupled to amine or thiol groups incorporated into a probe during synthesis. Labels can be coupled internally or to either terminus of a probe. A label(s) may be linked to a monomer unit of a probe via a spacer arm to reduce steric hindrance with, for example, hydrogen bond formation during probe hybridization. After synthesis, probes may be purified by high performance liquid chromatography (HPLC) or polyacrylamide gel electrophoresis (PAGE).

In certain embodiments a label may be incorporated into a precursor prior to the synthesis of a probe. Internal amino-modifications for labeling at "A" and "G" positions are also contemplated. Typically, when internal labeling is required, it is performed at a "T" position using a commercially available phosphoramidite. In certain embodiments library segments with a propylamine linker at the A and G positions are used to internally label a probe. The introduction of an internal aminoalkyl tail allows post-synthetic labeling of the probe. Linkers may be purchased from vendors such as Synthetic Genetics, San Diego, Calif.

In one embodiment automatic coupling using the appropriate phosphoramidite derivative of the label is also contemplated. These labels are coupled during the synthesis at the 5'-terminus.

1. Conductive Polymers

In certain embodiments conductive polymers may be used as a label. Conductive polymers are long, carbon-based chains composed of simple repeating units. Conductive polymers are generally formed by converting single-bond carbon chains to polymer backbones with alternating single and double bonds. This change typically provides a pathway for free-electron-charge carriers. Typical conductive-polymers include, but are not limited to polyaniline, polyphenylene-vinylene, polythiophene, polypyrrole, polyacetylene, polydiacetylene, polytriacetylene, poly-p-phenylene, polyfuran, betacarotene, substituted forms of these molecules and other similar conjugated oligomer materials. Conductive polymers may be composed of the same repeating unit (conductive polymer) or alternately different repeating units (conductive oligomer).

A. Tuning of Conductive Polymers

Optical transitions of conductive polymers may be tuned to certain emission spectra by the length and/or the composition of side chains of the conductive polymer. A non-limiting example is the alteration in the emission spectra of polyphenylene-vinylene (PPV) by alteration of side chains (R groups). Substitution of different side chains onto PPV, such as alkoxy groups will result in shift of the emission spectra to the red portion of the light spectrum. Substitution of an alkyl or an aryl side chain will lead to an emission shift to the blue end of the light spectrum.

By adjusting the length and/or side chain composition, the number of distinguishable conductive polymer labels may be very high—potentially in the tens of thousands or higher. Thus, conductive polymers may be of use in embodiments requiring large numbers of distinguishable label moieties.

B. Attachment of Conductive Polymers

Conductive polymers may be covalently attached to a probe. The probes may be oligonucleotides, PNAs or analogs thereof that hybridize sequence specifically to target nucleic acids. In general, the covalent attachments are made in such a manner as to minimize steric hindrance of a probe and any adjacent labels that may be attached to the same probe or adjacent probes. Linkers may be used that are generally short and provide a degree of flexibility to the label and labeled probe. In a certain embodiments the techniques outlined above may be used to attach a conductive polymer to nucleic acids and nucleic acid analogs, including PNAs.

The point of attachment to a base will vary with the base. While attachment at any position is possible, it is preferred to attach at positions not involved in hydrogen bonding to the complementary base. Thus, for example, attachment can be to the 5 or 6 positions of pyrimidines such as uridine, cytosine and thymine. For purines such as adenine and guanine, the linkage is preferably via the 8 position. Attachment to nonstandard bases is preferably done at the comparable positions.

In one embodiment, conductive polymers with terminal acetylene bonds may be attached directly to the base. Homo-or hetero-bifunctional linkers are available from various commercial sources. Linkers include, but are not limited to, alkyl groups and alkyl groups containing heteroatom moieties, with short alkyl groups, esters, epoxy groups and ethylene glycol and derivatives being preferred. Propyl, acetylene, and C2alkene groups are especially preferred. Linkers may also comprise a sulfone group, forming sulfonamide linkages. In particular embodiments, nucleosides may be modified with amino groups, sulfur groups, silicone groups, phosphorus groups, or oxo groups. These modified nucleosides are then used to attach the conductive polymers.

2. Fluorescent Labels

In certain embodiments fluorescent dyes may be used to label probes. Fluorophores include but are not limited to (Fluorophore (Excitation/Emission))—FAM (488 nm/518 nm); HEX (488 nm/556 nm); TET (488 nm/538 nm); CY (3550 nm/570 nm); CY5 (649 nm/670 nm); CY5.5 (675 nm/694 nm); JOE (527 nm/548 nm); 6-ROX (575 nm/602 nm); Cascadde Blue (400 nm/425 nm); Texas Red (595 nm/615 nm); Rhodamine (550 nm/575 nm); Rhodamine green (502 nm/527 nm); Rhodamine red (570 nm/590 nm); Rhodamine 6G (525 nm/555 nm); 6-TAMRA (555 nm/580 nm); 5-TAMRA (543 nm/567 nm); Alexa 430 (430 nm/545 nm); Alexa 488 (493 nm/516 nm); Alexa 594 (588 nm/612 nm); Bodipy R6G (528 nm/550 nm). These fluorescent labels are commercially available from a variety of vendors. Additional fluorescent labels include Tetramethyl rhodamine (argon laser), fluorscein, 9-carboxyethyl-6-hydroxy-3-oxo-3H-xanthene and its derivatives, 7-nitrobenzofurazan, and NBD. Xanthene dyes may be covalently attached through the carboxylic acid functionality, via an amide bond with a linker amine group. Fluorescent dyes may be used in conjunction with each other and/or quencher molecules to expand the number of spectrally unique labels. Other alternative labels or tags include semiconductor nanostructures or quantum dots that may be covalently attached to a probe.

Hybridization

Hybridization includes, but is not limited to forming a double stranded molecule or forming a molecule with a partial double stranded nature. In preferred embodiments, hybridization of the target nucleic acid to the probe library occurs under stringent conditions that allow hybridization between fully complementary nucleic acid sequences, but preclude hybridization between partially mis-matched sequences. For example, hybridization at low temperature and/or high ionic strength is termed low stringency. Hybridization at high temperature and/or low ionic strength is termed high stringency. Low stringency is generally performed at 0.15 M to 0.9 M NaCl at a temperature range of 20° C. to 50° C. High stringency is generally performed at 0.02 M to 0.15 M NaCl at a temperature range of 50° C. to 70° C.

It is understood that the temperature and/or ionic strength of a desired stringency are determined in part by the length of the particular probe, the length and/or base content of the target sequences, and the presence of formamide, tetrametylammonium chloride or other solvents in the hybridization mixture. Various standard hybridization solutions are well known. It is also understood that these ranges are mentioned by way of example only and that the desired stringency for a particular hybridization reaction is often determined empirically by comparison to positive and/or negative controls. Accordingly, the probes of the disclosure may be used for their ability to selectively form duplex molecules by hybridization with complementary stretches of target nucleic acids, such as DNA or RNA.

It is preferred to employ relatively stringent conditions to form hybridized nucleic acids comprising a target nucleic acid and one or more probe molecules. For example, relatively low salt and high temperature conditions, such as provided by about 0.02 M to about 0.10 M NaCl at temperatures of about 50° C. to about 70° C. Such high stringency conditions tolerate little, if any, mismatch between the probe and the target strand. It is generally appreciated that conditions may be rendered more stringent by the addition of increasing amounts of formamide or the like.

Processing of Hybridized Nucleic Acid Template

Once a target nucleic acid is hybridized to a probe library the hybridized nucleic acid will typically be processed. In certain embodiments non-hybridizing probes may be separated from a hybridized nucleic acid. A hybridized nucleic acid may be separated from non-hybridized probes before or after introduction into a microfluidic device. The separation of non-hybridized probes may be accomplished by, for example, selective precipitation, size exclusion columns, selective immobilization of a target nucleic acid or any equivalent technique.

A target nucleic acid may be immobilized in an input chamber of a microfluidic device by optical trapping, magnetic trapping, attachment to a chamber wall and similar immobilization methods. A target nucleic acid may be attached to an input chamber wall and subsequently hybridized to probe libraries. After incubation with an immobilized target nucleic acid non-hybridized probes can be washed out of an input chamber using inlet and outlet ports in a microfluidic device. Once separated from non-hybridized probes, a hybridized nucleic acid can be released from an input chamber wall and manipulated through a microchannel, microcapillary, or micropore for analysis. Alternatively, a hybridized nucleic acid that has been separated from non-hybridized probes by selective precipitation, size exclusion columns, or the like may be introduced into an input chamber and manipulated through a microchannel, microcapillary, or micropore for analysis.

Once non-hybridized probes are separated, a hybridized nucleic acid may be further manipulated by microfluidic sorting, fluidic focusing, or combinations thereof. Hydrodynamics on a micron scale can be used to manipulate the flow of nucleic acids into a microchannel, microcapillary, or a micropore and past a detector where the linear order of hybridized probes can be determined. In one embodiment of the invention microfluidics is used to sort hybridized nucleic acid(s). Microfluidic sorting of hybridized nucleic acids may include filtering of a solution containing hybridized nucleic acids across a comb to separate individual molecules which are subsequently moved into a microchannel, microcapillary, or a micropore one or more molecule at a time. Manipulation of the fluid flow may be done by using electric, thermal, pressure or vacuum motive forces.

In another embodiment microfluidics is used to fluidically focus hybridized nucleic acid(s). Fluidic focusing of hybridized nucleic acids may include moving a fluid containing hybridized nucleic acids through a narrowing path at an appropriate velocity to produce a focused stream of fluid flow, thus separating individual molecules and moving the molecules into a microchannel, microcapillary, or a micropore one or more molecule at a time. Manipulation of the fluid flow may be done by using electric, thermal, pressure or vacuum motive forces.

1. Microfluidics

Microfluidics is defined as the domain of fluidics where the fluids have a Reynolds number much smaller than one, which implies that the fluid flow is laminar. A Reynolds number (Re) is a dimensionless number used in fluid dynamics to describe the nature of fluid flow in a particular situation: Reynolds number=density×flow velocity× characteristic dimension/viscosity. At low Re the viscous forces dominate and extend over large distances causing laminar flow. In most practical cases, these low Reynolds numbers require the channels in which the fluid flows to measure in the tens of micrometers range or less.

The small dimensions also require precise dimensional control, since the fluidic properties are very sensitive to dimensional variations. When precise dimensional control is required, silicon is an excellent material for construction. Photolithography techniques used in integrated circuit processing have been used with this material to obtain channels in the range of tens of micrometers wide and deep.

The microfluidic devices of certain embodiments comprise a central body structure in which the various microfluidic elements are disposed. The body structure includes an exterior portion or surface, as well as an interior portion that defines the various microscale channels and/or chambers of the overall microfluidic device. For example, the body structures of a microfluidic device typically employ a solid or semisolid substrate that is typically planar in structure, i.e., substantially flat or having at least one flat surface. Often, the planar substrates are manufactured using solid substrates common in the fields of microfabrication, e.g., silica-based substrates, such as glass, quartz, silicon or polysilicon, as well as other known substrates, i.e., gallium arsenide. In the case of these substrates, common microfabrication techniques, such as photolithographic techniques, wet chemical etching, micromachining, i.e., drilling, milling and the like, may be readily applied in the fabrication of microfluidic devices and substrates. Alternatively, polymeric substrate materials may be used to fabricate the devices of the present invention, including, e.g., polydimethylsiloxanes (PDMS), polymethylmethacrylate (PMMA), polyurethane, polyvinylchloride (PVC), polystyrene polysulfone, polycarbonate, polymethylpentene, polypropylene, polyethylene, polyvinylidine fluoride, ABS (acrylonitrile-butadiene-styrene copolymer), and the like. In the case of such polymeric materials, injection molding or embossing methods may be used to form the substrates having the channel and reservoir geometries as described herein.

The channels and chambers of the device are typically fabricated into one surface of a planar substrate, as grooves, wells or depressions in that surface. A second planar substrate, typically prepared from the same or similar material, is overlaid and bonded to the first, thereby defining and sealing the channels and/or chambers of the device. Together, the upper surface of the first substrate, and the lower mated surface of the upper substrate define the channels and chambers of the device.

Movement of fluids through the device will typically be regulated by computer-controlled pressure and electrokinetic forces to gain exact control over the flow of fluids in microfluidic channels. Typically, electricity is used to drive samples through the channels. In one form of stimulation, electro-osmosis, computer-driven power supplies located in reservoirs at each end of a channel are activated to generate electrical current through the channel. The current forces molecules with different electrical charges in fluids to travel through the channels at different rates; a typical speed is one millimeter per second. Another type of electrokinesis—electrophoresis—is simply a microminiaturized version of an analytical approach routinely used in chemistry laboratories. An electric field influences the movement of charged molecules in microfluids moving through the channels. Electric fields can be used to move molecules in solution or to separate molecules with very subtle differences.

Alternate methods for moving microfluids include temperature gradients or micropressure. For example, small amounts of pressure applied to microfluids traveling through channels create predictable and reproducible flows. Temperature gradients can move tiny volumes of liquids around nano-sized canals in silicon wafers. This occurs because the surface tension of the microfluids varies with temperature; a temperature gradient of just three or four degrees Celsius is enough to cause a microfluid to seek a cold region in its pathway. Chemical modifications to the substrate applied by lithography amplify the effect by creating a series of chemical levees along the canals.

Optical Trapping

In alternative embodiments an optical trap can be used to manipulate a target nucleic acids. An optical trap is a device in which a particle can be trapped near the focus of a strongly focused light beam such as a laser beam. The particle is held in the trap by the axial gradient force that is proportional to the gradient of the light intensity and points in the direction of increased intensity. In general, single-beam optical trapping can be achieved for particles having sizes ranging from about 10 μm to about 10 nm. Commercial optical trapping systems are available, such as, LaserTweezers(tm) 2000, Cell Robotics, inc.; Compact Photonic Tweezers, S+L Gmb; and PALM(tm) Laser-Microscope System, P.A.L.M. GmbH. In certain embodiments a target nucleic acid may be immobilized onto a bead. The bead can then be optically trapped within a hybridization chamber of a microfluidic device. Alternatively, a target nucleic acid may be immobilized onto a magnetic bead that is subsequently trapped magnetically.

Methods of Nucleic Acid Immobilization

In various embodiments, the nucleic acid molecules of the present invention may be attached or immobilized to a solid surface. Immobilization of nucleic acid molecules may be achieved by a variety of methods involving either non-covalent or covalent attachment between the nucleic acid molecule and a support or surface. In an exemplary embodiment, immobilization may be achieved by coating a solid surface with streptavidin or avidin and the subsequent attachment of a biotinylated polynucleotide. Immobilization may also occur by coating a polystyrene, glass or other solid surface with poly-L-Lys or poly L-Lys, Phe, followed by covalent attachment of either amino- or sulfhydryl-modified nucleic acids using bifunctional crosslinking reagents. Amine residues may be introduced onto a surface through the use of aminosilane.

Immobilization may take place by direct covalent attachment of 5'-phosphorylated nucleic acids to chemically modified polystyrene surfaces. The covalent bond between the nucleic acid and the solid surface is formed by condensation with a water-soluble carbodiimide. This method facilitates a predominantly 5'-attachment of the nucleic acids via their 5'-phosphates.

DNA is commonly bound to glass by first silanizing the glass surface, then activating with carbodiimide or glutaraldehyde. Alternative procedures may use reagents such as 3-glycidoxypropyltrimethoxysilane (GOP) or aminopropyltrimethoxysilane (APTS) with DNA linked via amino linkers incorporated either at the 3' or 5' end of the molecule during DNA synthesis. DNA may be bound directly to membranes using ultraviolet radiation. Other non-limiting examples of immobilization techniques for nucleic acids are known.

The type of surface to be used for immobilization of the nucleic acid is not limited to those disclosed above. In various embodiments, the immobilization surface could be magnetic beads, non-magnetic beads, a planar surface, a pointed surface, or any other conformation of solid surface comprising almost any material, so long as the material will allow hybridization of target nucleic acids to probe libraries.

Bifunctional cross-linking reagents may be of use in various embodiments, such as attaching a nucleic acid molecule to a surface. Exemplary cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

In certain embodiments a capture oligonucleotide may be bound to a surface. The capture oligonucleotide will hybridize with a specific nucleic acid sequence of a target nucleic acid. Once a target nucleic acid is hybridized to a capture oligo it may be covalently attached by a ligation reaction. A target nucleic acid may be released from the surface by restriction enzyme digestion, elevated temperature, reduced salt concentration, or a combination of these and similar methods.

Detection Unit

In particular embodiments a detection unit may comprise an excitation source and a detector. An excitation source can promote alterations in a label that can result in a signal emission. For example, an electron beam may excite electrons of a label by coulombic induction, which may result in a fluorescent emission as an excited label returns to its ground state. Emitted energy can be detected by a variety of detectors including, but not limited to microspectrophotometers, photomultiplier tubes and avalanche detectors. In a particular embodiment a micro electron beam may be used as an excitation source. Preferably, the energy absorbed will be emitted as a detectable signal and each label will have a unique spectral profile.

Excitation Source

In certain embodiments the excitation source can be an electron beam. In alternate embodiments the excitation source may generate other forms of electromagnetic radiation such as UV, visible or infrared light. Alternate embodiments rely on detection and identification of probes released after transit through a microchannel, microcapillary, or micropore by hybridization to arrays, mass spectroscopy or nuclear magnetic resonance. Probes may be released from a target nucleic acid after transit through a microfluidic device by enzymatic degradation of a target nucleic acid or disruption of the sequence specific binding of the probe to the target nucleic acid, for example by heating. Released probes can be further manipulated by flow through an extended microfluidic device to an appropriate detector.

Figure 5:
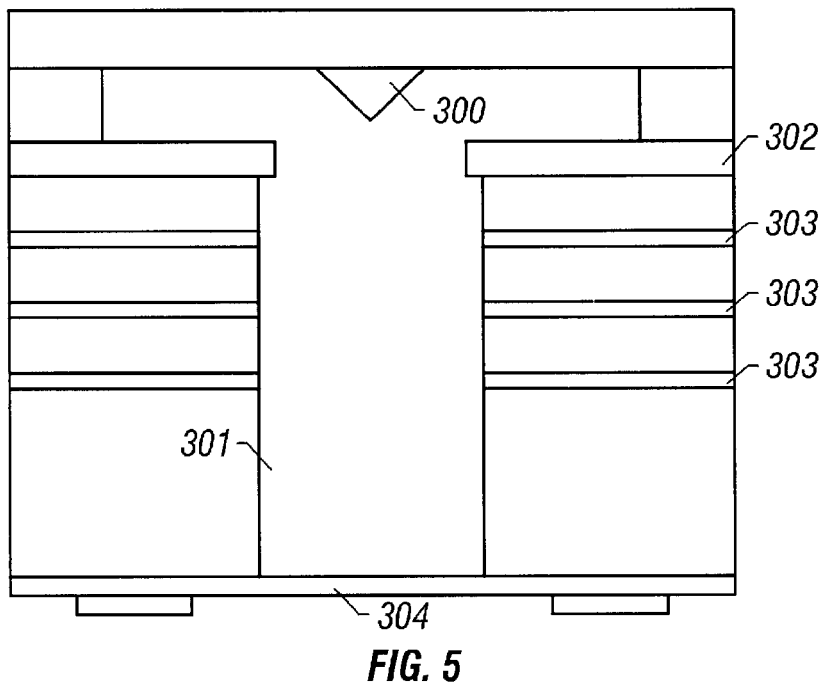
FIG. 5 illustrates one embodiment of a micro column electron beam source.

In certain embodiments the excitation source may be a micro column electron beam (micro e-beam) source as illustrated in FIG. 5. The excitation source illustrated in FIG. 5 may be made by using microfabrication techniques known in the art and is based largely on the micromachining of silicon. The stacked parts of the device would be assembled in a vacuum using a wafer-to-wafer bonding approach. An electron source 300 is positioned at the opening of an evacuated column 301. The opening of the evacuated column 301 has an associated low-voltage gate electrode 302. Perpendicular to the evacuated column's long axis are aligned high-voltage acceleration, deflection, and focusing electrodes 303. The evacuated column is typically sealed at the far end by an electron transparent membrane 304 that is typically operatively coupled to a microchannel. The electron transparent membrane 304 is positioned so that an electron beam can be focused onto a channel. The channel provides a microfluidic path for the passage of target nucleic acids hybridized to labeled probes. The e-beam can be directed so it is incident with passing target nucleic acid(s) and excites an associated labeled probe. The excited label typically emits spectra of light characteristic of the probe. Photons of light are detected by a detector array and may be stored in a processing unit for further analysis.

Figure 6:
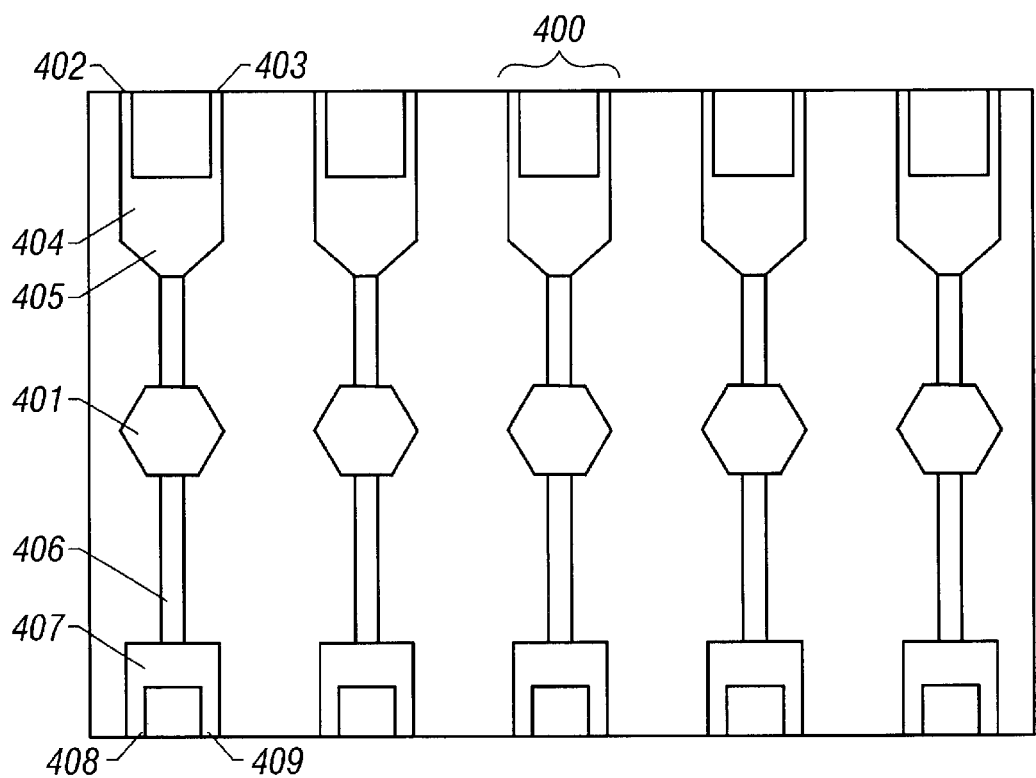
FIG. 6 illustrates one embodiment of an array of microfluidic sequencing units.

In one embodiment an array of micro column electron beam sources may be fabricated onto a support. FIG. 6 shows an array of microfluidic electron induced fluorescence sequencing apparatus 400. Each of the microfluidic devices comprises a micro column electron beam source 401, an inlet port 402, an outlet port 403, an input chamber 404, fluidic focusing region 405, microchannel 406, an output chamber 407, inlet exit port 408 and an outlet exit port 409. The input chamber 404 is in fluid communication with the output chamber 407 via the microchannel 406. A single hybridization mixture can be introduced to and analyzed in each device 400 of the array. Alternatively, distinct hybridization mixtures can be introduced to and analyzed in separate devices 400 of the array.

Signal Detection

Signals produced by one or more labeled probes may be detected by various detection means. In certain embodiments the energy released by a label can be detected using sensitive detection means such as a spectrophotometer, photomultiplier tube, charge-coupled device, or avalanche photodiode. In particular embodiments light emitted by a label can be analyzed by a Jobin-Yvon HRD1 double grating monochromator and detected by a GaAs cathode photomultiplier tube, then fed to a computer through a photon counter. Alternatively, the detectors may be used in conjunction with fluorescent microscopy.

Determination of Nucleic Acid Sequence

In one embodiment a nucleic acid sequence may be determined by using a decoding method. In certain embodiments, a decoding method, as illustrated by the flow chart in FIG. 4, may entail the immobilization a single stranded DNA or a double stranded DNA 200 followed by denaturation to provide a target single-stranded nucleic acid sequence. A probe library or a plurality of probe libraries may be created 201 such that each probe of the library will have an associated label that will specifically and uniquely identify the probe. The target nucleic acid sequence is incubated with a probe library or series of probe libraries to allow hybridization of the probes to the target sequence 202. After hybridization of the probes the hybridized nucleic acids are manipulated through a micro-fluidic channel where they flow past an excitation source and a detector 203. Emission spectra of the labeled probes may then be detected and relayed to a data processing system 204. The sequence of the target nucleic acid is determined by comparing the emission spectra and the order in which the emission spectra were detected to a database of spectra for labels associated with the probes 205. The linear sequence of probes hybridized to the target nucleic acid can then be determined by either statistical calculations or the determination of probe order from a single target nucleic acid molecule.

In alternate embodiments of the invention individual probes hybridized to the target nucleic acid may be covalently joined to adjacent probes by ligation. Ligation of probes would produce longer segments of hybridized sequences and a more stable association between probe and target. The data collected may be analyzed and translated into the target nucleic acid sequence by using a computer implemented system designed for such analysis.

The length of nucleic acid analyzed by this method should only be limited by the length of nucleic acid that can be manipulated with out shearing, breaking or other means of degradation of a target nucleic acid, allowing for extended read lengths and faster, more economical sequencing of nucleic acids.

Information Processing and Control System and Data Analysis

In certain embodiments, the sequencing apparatus may be interfaced with an information processing and control system. In an exemplary embodiment, the system incorporates a computer comprising a bus or other communication means for communicating information, and a processor or other processing means coupled with the bus for processing information. In one embodiment, the processor is selected from the Pentium® family of processors, including the Pentium® II family, the Pentium® III family and the Pentium® 4 family of processors available from Intel Corp. (Santa Clara, Calif.). In alternative embodiments, the processor may be a Celeron®, an Itanium®, or a Pentium Xeon® processor (Intel Corp., Santa Clara, Calif.). In various other embodiments, the processor may be based on Intel® architecture, such as Intel® IA-32 or Intel® IA-64 architecture. Alternatively, other processors may be used.

The computer may further comprise a random access memory (RAM) or other dynamic storage device (main memory), coupled to the bus for storing information and instructions to be executed by the processor. Main memory may also be used for storing temporary variables or other intermediate information during execution of instructions by processor. The computer may also comprise a read only memory (ROM) and/or other static storage device coupled to the bus for storing static information and instructions for the processor. Other standard computer components, such as a display device, keyboard, mouse, modem, network card, or other components known in the art may be incorporated into the information processing and control system. The skilled artisan will appreciate that a differently equipped information processing and control system than the examples described herein may be desirable for certain implementations. Therefore, the configuration of the system may vary within the scope of the present invention.

In particular embodiments, the detection unit may also be coupled to the bus. Data from the detection unit may be processed by the processor and the processed and/or raw data stored in the main memory. Data on known emission spectra for labeled probes may also be stored in main memory or in ROM. The processor may compare the emission spectra from probes in the channel to the stored spectra to identify the sequence of probes passing along the channel. The processor may analyze the data from the detection unit to determine the sequence of the target nucleic acid.

The information processing and control system may further provide automated control of the sequencing apparatus. Instructions from the processor may be transmitted through the bus to various output devices, for example to control the pumps, electrophoretic or electro-osmotic leads and other components of the apparatus.

It should be noted that, while the processes described herein may be performed under the control of a programmed processor, in alternative embodiments, the processes may be fully or partially implemented by any programmable or hardcoded logic, such as Field Programmable Gate Arrays (FPGAs), TTL logic, or Application Specific Integrated Circuits (ASICs), for example. Additionally, the method of the present invention may be performed by any combination of programmed general purpose computer components and/or custom hardware components.

In certain embodiments, custom designed software packages may be used to analyze the data obtained from the detection unit. In alternative embodiments, data analysis may be performed using an information processing and control system and publicly available software packages. Non-limiting examples of available software for DNA sequence analysis includes the PRISM™ DNA Sequencing Analysis Software (Applied Biosystems, Foster City, Calif.), the Sequencher™ package (Gene Codes, Ann Arbor, Mich.), and a variety of software packages available through the National Biotechnology Information Facility at website www.nbif.org/links/1.4.1.php.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Probe Library

Oligonucleotides are either purchased from vendors such as Genetic Designs, Inc. Houston, Tex. or made on an Applied Biosystems 381A DNA synthesizer. The probe library ia synthesized using nucleotide or nucleotide analogs that have been covalently modified with a conductive polymer, with each probe incorporating a unique conductive polymer.

Reliable hybridizations are obtained with probes six to eight nucleotides in length. These procedures allow maximal reduction in the number of probes per library, reducing the costs of sequencing reaction. A complete library of 4,096 random hexamers, each labeled with a unique conductive polymer label is synthesized as described above. Label moieties are covalently attached to a nucleotide precursor prior to probe synthesis. Each probe is labeled at the 3' end with a single label moiety.

Example 2

Hybridization Procedures

Target DNA is immobilized by optical trapping in an input chamber of a microfluidic device. The input chamber is filled with a hybridization solution (0.5M Na2 HPO4, pH 7.2, 7% sodium lauroyl sarcosine). A hexamer probe library as described above is added and allowed to hybridize to the target nucleic acid by incubation at 60° C. for 1 hr. Probe concentration is 10 µg of DNA in 100 µl of hybridization solution. Hybridization is stopped by the introduction of 6× SSC washing solution and non-hybridized probes are removed by washing multiple times. The target nucleic acid is released from the optical trap and enters the channel for detection of hybridized probes.

Example 3

Analysis of Bound Probes

The hybridized nucleic acid is released from the chamber and an electro-osmotic motive force is applied, driving the hybridized nucleic acid down the channel past the detection unit. As each probe passes the microelectron beam and microspectrophotometer the fluorescence of the associated label is detected as a spectral profile, which is associated with a particular probe of known sequence. The linear order of probe molecules is assembled by the analysis of multiple hybridizations. Once the linear order of probes is obtained the target nucleic acid sequence is be determined.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A nucleic acid sequencing apparatus comprising:
   a) an input chamber;
   b) a microchannel in fluid communication with the input chamber; and
   c) a detection unit operably coupled to the microchannel, the detection unit comprising a detector and a micro column electron beam source comprising:
      an electron source positioned at the opening of an evacuated column;
      a low-voltage gate electrode at the opening of the evacuated column;
      aligned high-voltage acceleration, deflection and focusing electrodes perpendicular to the long axis of the evacuated column; and
      an electron transparent membrane to seal the far end of the evacuated column.

2. The apparatus of claim 1, further comprising an information processing and control system operably coupled to the detector.

3. The apparatus of claim 1, further comprising a fluidic focusing region between the input chamber and the microchannel.

4. The apparatus of claim 1, further comprising a target nucleic acid hybridized to multiple labeled probes, each probe distinguishably labeled.

5. The apparatus of claim 4, wherein the probes are labeled with conductive polymer molecules.

6. The apparatus of claim 3, wherein the fluidic focusing region contains a separating comb.

7. The apparatus of claim 1, further comprising an array of microfluidic sequencing units.

8. The apparatus of claim 5, wherein the conductive polymer molecules are selected from the group consisting of polyaniline, polyphenylene-vinylene, polythiophene, polypyrrole, polyacetylene, polydiacetylene, polytriacetylene, poly-p-phenylene, polyfuran, betacarotene, a substituted polyaniline, a substituted polyphenylene-vinylene, a substituted polythiophene, a substituted polypyrrole, a substituted polyacetylene, a substituted polydiacetylene, a substituted polytriacetylene, a substituted poly-p-phenylene, a substituted polyfuran, a substituted betacarotene and a conjugated oligomer.

9. The apparatus of claim 8, wherein the substitution is an alkoxy side chain, an alkyl side chain or an aryl side chain.

10. The apparatus of claim 1, wherein said electron transparent membrane is positioned so that an electron beam can be focused onto the microchannel coupled to the membrane.

11. The apparatus of claim 10, wherein said detection unit comprises an array of optical detectors.

12. The apparatus of claim 7, wherein each microfluidic sequencing unit comprises:

a micro column electron beam source;

inlet and outlet ports;

input and output chambers;

a fluidic focusing region;

a microchannel; and inlet and outlet exit ports.

13. The apparatus of claim 1, wherein said detector comprises a spectrophotometer, photomultiplier tube, charge-coupled device, avalanche photodiode or double grating monochromator.

* * * * *